(12) United States Patent
Kawasaki et al.

(10) Patent No.: US 6,707,484 B1
(45) Date of Patent: Mar. 16, 2004

(54) INFORMATION PROCESSING SYSTEM

(75) Inventors: Yuji Kawasaki, Kanagawa (JP); Jun Koyama, Kanagawa (JP); Futoshi Ishi, Kanagawa (JP); Shunpei Yamazaki, Tokyo (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 0 days.

(21) Appl. No.: 09/382,676

(22) Filed: Aug. 25, 1999

Related U.S. Application Data

(62) Division of application No. 08/505,947, filed on Jul. 24, 1995, now Pat. No. 6,307,948.

(30) Foreign Application Priority Data

Jul. 28, 1994 (JP) .............................................. 6-198044

(51) Int. Cl.⁷ ................................................. H04N 7/14
(52) U.S. Cl. ............................... 348/14.01; 348/14.08; 379/93.17
(58) Field of Search ............................ 348/14.01, 14.02, 348/14.04, 14.05, 14.07, 14.08, 14.1; 379/93.21, 93.17; 381/100; H04N 7/14, 7/15

(56) References Cited

U.S. PATENT DOCUMENTS

| | | | |
|---|---|---|---|
| 4,359,724 A | 11/1982 | Zimmerman et al. | ....... 340/575 |
| 4,533,943 A | 8/1985 | Poirier | |
| 4,645,872 A | 2/1987 | Pressman et al. | |
| 4,706,072 A | 11/1987 | Ikeyama | ..................... 340/575 |
| 4,755,045 A | 7/1988 | Borah et al. | |
| 4,789,235 A | 12/1988 | Borah et al. | |
| 4,827,532 A | 5/1989 | Bloomstein | |
| 4,859,050 A | 8/1989 | Borah et al. | |
| 4,928,090 A | 5/1990 | Yoshimi et al. | ............. 340/575 |
| 4,928,300 A | 5/1990 | Ogawa et al. | |
| 4,953,111 A | 8/1990 | Yamamoto et al. | |
| 5,008,946 A | 4/1991 | Ando | ......................... 382/104 |
| 5,046,835 A | 9/1991 | Billeter et al. | .............. 351/206 |
| 5,057,834 A | 10/1991 | Nordstrom | |
| 5,065,447 A | 11/1991 | Barnsley et al. | |
| 5,079,627 A | 1/1992 | Filo | |
| 5,086,480 A | 2/1992 | Sexton | |
| 5,293,427 A | 3/1994 | Ueno et al. | ................. 382/103 |
| 5,381,195 A | 1/1995 | Rootzen et al. | |
| 5,402,109 A | 3/1995 | Mannik | |
| 5,412,708 A | 5/1995 | Katz | ........................... 348/14 |
| 5,465,079 A | 11/1995 | Bouchard et al. | |
| 5,537,662 A | 7/1996 | Sato et al. | |

(List continued on next page.)

FOREIGN PATENT DOCUMENTS

| | | |
|---|---|---|
| EP | 0 240 336 | 10/1987 |
| EP | 0 571 934 | 12/1993 |
| JP | 62-217939 | 9/1987 |

(List continued on next page.)

OTHER PUBLICATIONS

Harasaki et al. "Background Separation / Filtering for Videophone Applications", IEEE 1990, pp. 1981–1984.

*Primary Examiner*—Melur Ramakrishnaiah
(74) *Attorney, Agent, or Firm*—Eric J. Robinson; Robinson Intellectual Property Law Office, P.C.

(57) ABSTRACT

In an information processing system provided with a camera and a microphone, for transmitting and receiving information of a user to and from another information processing system through a transmission lime, image data of the user obtained by a camera is stored in a memory in advance. When one user communicates another user, image data of the one user is obtained by the camera and is synthesized with the image data stored in the memory in advance by image-processing. The clothes, hair, background, make-up etc. of the one user are made different to reality and the image data are transmitted to the another user in the communication.

29 Claims, 7 Drawing Sheets

U.S. PATENT DOCUMENTS

| | | |
|---|---|---|
| 5,541,640 A | 7/1996 | Larson |
| 5,585,839 A | 12/1996 | Ishida et al. .................. 248/15 |
| 5,606,361 A | 2/1997 | Davidsohn et al. |
| 5,611,038 A | 3/1997 | Shaw et al. |
| 5,734,923 A | 3/1998 | Sagawa et al. |

FOREIGN PATENT DOCUMENTS

| | | | | | |
|---|---|---|---|---|---|
| JP | 62-245183 | | 10/1987 | | |
| JP | 402238788 | * | 9/1990 | ............ | H04N/7/15 |
| JP | 403049492 A | * | 3/1991 | ............ | H04N/7/14 |
| JP | 03-255793 | | 11/1991 | | |
| JP | 404310086 A | * | 11/1992 | ............ | H04N/7/14 |
| JP | 05-294166 | | 11/1993 | | |
| JP | 06-046414 | | 2/1994 | | |
| JP | 406038205 A | * | 2/1994 | ............ | H04N/7/15 |
| JP | 06-070313 | | 3/1994 | | |
| JP | 406070313 A | * | 3/1994 | ............ | H04N/7/14 |
| JP | 406141308 A | * | 5/1994 | ............ | H04N/7/14 |
| JP | 406205404 A | * | 7/1994 | ............ | H04N/7/14 |
| KR | 89-000903 | | 7/1989 | | |
| KR | 88-000903 | | 3/1998 | | |

\* cited by examiner

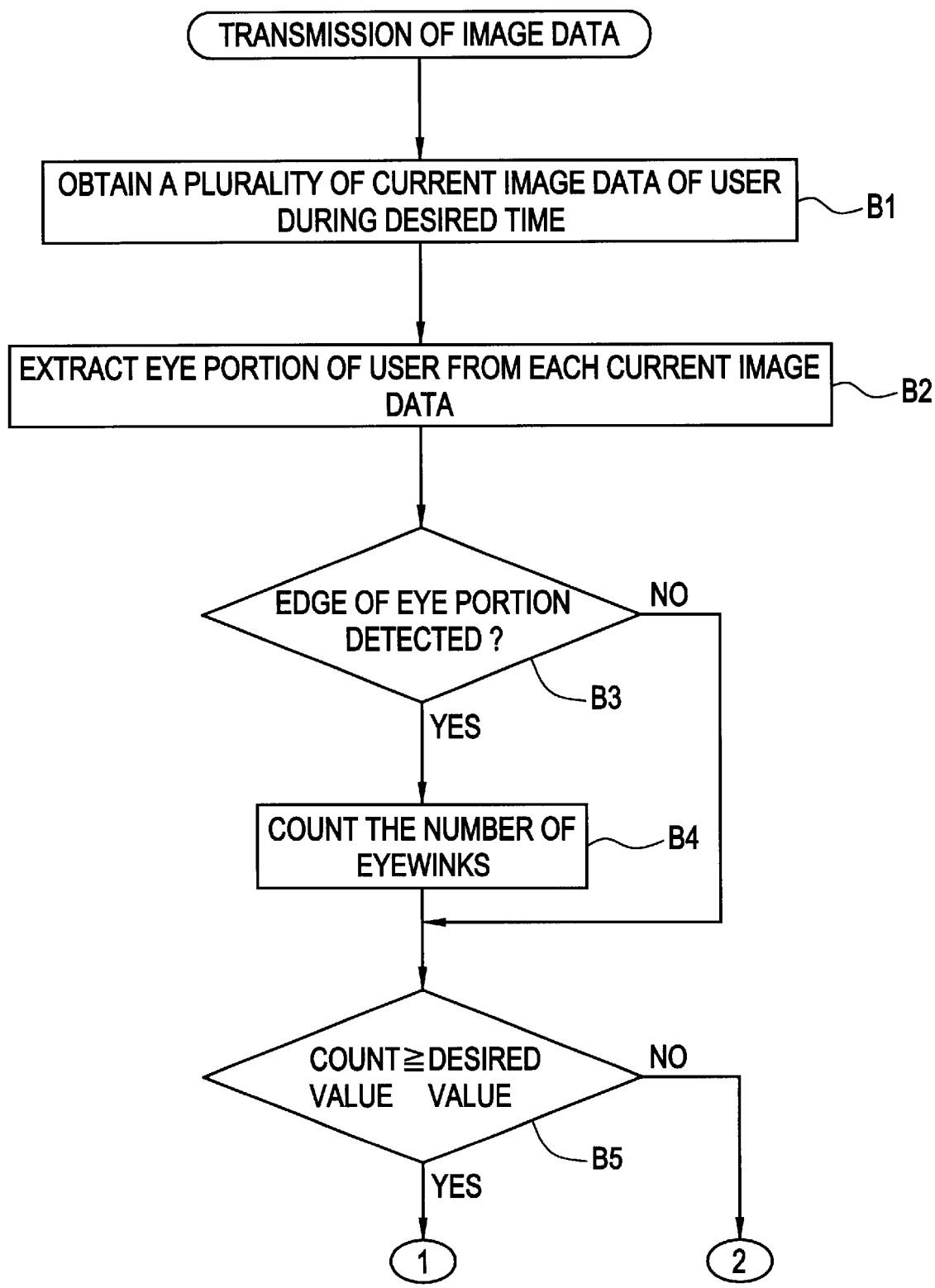

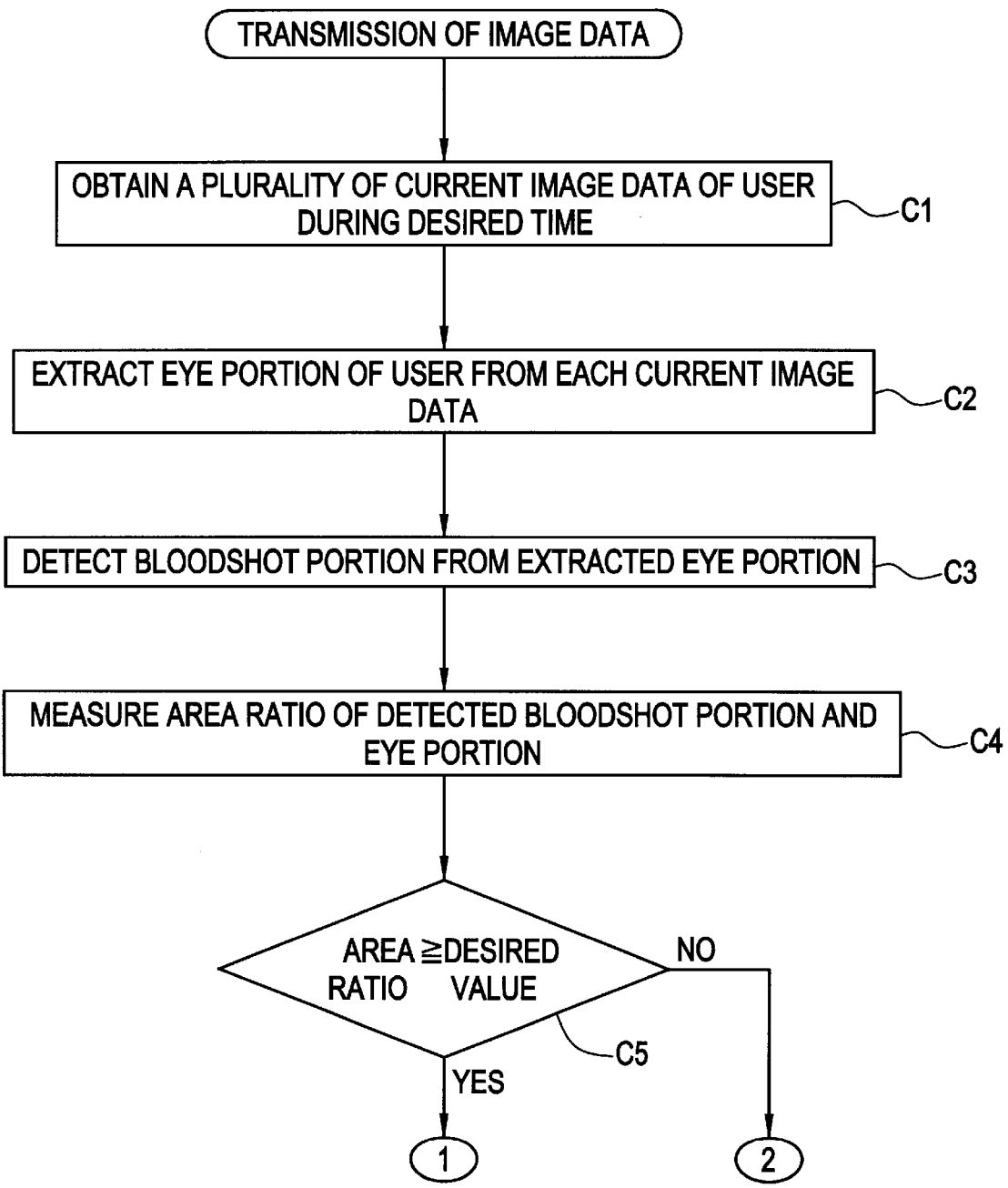

INFORMATION PROCESSING SYSTEM

This application is a Divisional of application Ser. No. 08/505,947, filed Jul. 24, 1995.

BACKGROUND OF THE INVENTION

1. Field of the Invention

The present invention relates to an information processing system which is provided with a camera and a microphone and transmits/receives image data and voice (sound) data of the users to/from another information processing system through a transmission line.

2. Description of the Related Art

There have been known information processing systems for transmitting and receiving image data and voice data via a communication line using, as terminals, information processing systems provided with a camera and a microphone, such as communication using videophones or computers.

With these information processing systems, not only voice can be transmitted, but the conversing parties can also talk while looking at each other's face expression, and further images such as characters or photographs can also be transmitted, and it is therefore possible to transmit and receive a larger volume of data than with voice only, and thus detailed and profound conversations can be held.

With these information processing systems, image data of both of the communicating parties are transmitted, regardless of the intention of the conversing parties. Thus, before the parties involved in the communication communicate with each other, it is often necessary to perform operations which are not necessary for the transmission, such as arranging one's appearance and tidying the surroundings.

Simplicity of transmission is therefore lost. Further, there is a deficiency in terms of maintaining the privacy of the receiving party since, in comparison with the calling party who has, in advance, been intending to have a conversation, the receiving party may not have made sufficient preparation for the conversation.

In other words, with conventional data communication involving voice and images, the appearance of the users is transmitted directly as image data to the other party, and therefore if it is necessary to communicate when the receiving party of the communication does not wish to do so, the receiving party is subjected to psychological anguish.

If the receiving party is compelled, having just woken up, to communicate using an information processing system provided with a camera and a microphone, that is, if, clothes, hair or make-up, the surroundings and the like are in disarray, such that the receiving party would be impolite to the other party to appear, or if the receiving party were extremely tired and the expression was likely to become gloomy, the receiving party would be forced to refuse to send to the other party the image data of the receiving party, which had been taken by the camera, and thus to refuse to transmit image data.

Thus to protect the minimal privacy of the receiving party of the communication, transmission of image data is stopped and communication of only voice data is performed. Therefore the services using information communication of image and voice are not effectively utilized.

Further, if there is a sudden need for the calling party to transmit information, then even the receiving party may decide to refrain from effecting communication that is accompanied by the transmission of images, unless the receiving party has arranged so as not to appear impolite to the other party, and tidied the surroundings, and thus in the end there is a likelihood that the matter will be dealt with using a normal voice-only telephone or a facsimile.

SUMMARY OF THE INVENTION

The object of the present invention is to provide an image processing system whereby, when image data and voice data are being transmitted and received using an information processing system provided with a camera and a microphone, conversation is possible using images and voice (sound) without the transmission of image data which the transmitting party does not wish to be transmitted.

In order to solve the above problem, one of the main inventions disclosed in the present specification is an information processing system for transmitting and receiving information of a user to and from another information processing system through a transmission line, the system comprising, a camera for obtaining image data of the user, a microphone for obtaining voice (sound) data of the user, means for image-processing the image data, to obtain different image data in portions other than a face of the user, and means for transmitting the image-processed image data and the obtained voice data to the another information processing system. In the construction, portions other than the face correspond to the background, clothes, hair, portions below the neck and the like.

Further, one important construction disclosed in the present specification is An information processing system for transmitting and receiving information of a user to and from another information processing system through a transmission line, the system comprising, a camera for obtaining one image data representing an expression of the user, a microphone for obtaining voice data of the user, means for changing the one image data for another image data or synthesizing the one image data with another image data, and means for transmitting the changed or synthesized image data and the voice data to the another information processing system.

Further, one important construction disclosed in the present specification is an information processing system for transmitting and receiving information of a user to and from another information processing system through a transmission line, the system comprising, a camera for obtaining one image data representing an expression of the user and another image data representing a movement of a mouth of the user, a microphone for obtaining voice data of the user, means for storing the one image data in advance, means for synthesizing the stored one image data with the another image data, and means for transmitting the synthesizing image data and the voice data to the another information processing system.

Further, one important construction disclosed in the present specification is an information processing system for transmitting and receiving information of a user to and from another information processing system through a transmission line, the system comprising, a camera for obtaining one image data representing an expression of a face of the user and another image data representing a movement of a mouth of the user, a microphone for obtaining voice data of the user, means for storing the one image data in advance, means for detecting a degree of tiredness of the user by image-processing the stored one image data, and changing the stored one image data for synthesizing image data in accordance with the degree of tiredness of the user, wherein the synthesizing image data is obtained by synthesizing the stored one image data with the another image data, and means for transmitting the voice data and one of the stored one image data and the synthesizing image data to the another information processing system.

Further, one important construction disclosed in the present specification is an information processing system for transmitting and receiving information of a user to and from another information processing system through a transmission line, the system comprising, a camera for obtaining one image data representing an expression of a face of the user and another image data representing a movement of a mouth of the user, a microphone for obtaining voice data of the user, means for storing the one image data in advance, means for detecting a degree of tiredness of the user by image-processing the stored one image data and changing the stored one image data for synthesizing image data in accordance with the degree of tiredness of the user, wherein the synthesizing image data is obtained by synthesizing the stored one image data with the another image data, and means for transmitting the voice data and one of the stored one image data and the synthesizing image data to the another information processing system, wherein the degree of tiredness of the user is obtained by measuring the number of blinks of the user per unit time in accordance with the one image data, and comparing the number of the blinks of the user with a reference blink value representing the reference number of blinks of the user per unit time, measured in advance.

Further, one important construction disclosed in the present specification is an information processing system for transmitting and receiving information of a user to and from another information processing system through a transmission line, the system comprising, a camera for obtaining one image data representing an expression of a face of the user and another image data representing a movement of a mouth of the user, a microphone for obtaining voice data of the user, means for storing the one image data in advance, means for detecting a degree of tiredness of the user by image-processing the stored one image data, and changing the stored one image data for synthesizing image data in accordance with the degree of tiredness of the user, wherein the synthesizing image data is obtained by synthesizing the stored one image data with the another image data, and means for transmitting the voice data and one of the stored one image dada and the synthesizing image data to the another information processing system, wherein the degree of tiredness of the user is obtained by measuring the number of blinks of the user per unit time and identifying the user in accordance with the one image data, referring to a reference blink value of the user in accordance with the identification, and comparing the number of the blinks of the user with the reference blink value of the user, the reference blink value representing the reference number of blinks of the user per unit time, measured in advance.

Further, one important construction disclosed in the present specification is an information processing system for transmitting and receiving information of a user to and from another information processing system through a transmission line, the system comprising, a camera for obtaining one image data representing an expression of a face of the user and another image data representing a movement of a mouth of the user, a microphone for obtaining voice data of the user, means for storing the one image data in advance, means for detecting a degree of tiredness of the user by image-processing the stored one image data, and changing the stored one image data for synthesizing image data in accordance with the degree of tiredness of the user, wherein the synthesizing image data is obtained by synthesizing the stored one image data with the another image data, and means for transmitting the voice data and one of the stored one image data and the synthesizing image data to the another information processing system, wherein the degree of tiredness of the user is obtained by measuring the number of blinks of the user per unit time and identifying the user with an ID number, referring to a reference blink value of the user in accordance with the identification, and comparing the number of the blinks of the user with the reference blink value of the user, the reference blink value representing the reference number of blinks of the user per unit time, measured in advance.

To elaborate, one of the important inventions disclosed by the present specification is an information processing system (for example, a personal computer or videophone connected to a transmission line) provided with a camera and a microphone, wherein the number of blinks of the user is obtained from image data taken in by the camera, and the degree of tiredness of the user is estimated by calculating the number of blinks per unit time using an internal timing circuit; if this exceeds a certain fixed value, the actual image data of the user are not transmitted but image data which are a combination of the movement of the mouth of the user with image data which have been taken and stored in advance are transmitted.

Further, one important construction disclosed in the present specification is an information processing system for transmitting and receiving information of a user to and from another information processing system through a transmission line, the system comprising, a camera for obtaining one image data representing an expression of a face of the user and another image data representing a movement of a mouth of the user, a microphone for obtaining voice data of the user, means for storing the one image data in advance, means for detecting a degree of tiredness of the user by image-processing the stored one image data, and changing the stored one image data for synthesizing image data in accordance with the degree of tiredness of the user, wherein the synthesizing image data is obtained by synthesizing the stored one image data with the another image data, and means for transmitting the voice data and one of the stored one image data and the synthesizing image data to the another information processing system, wherein the degree of tiredness of the user is obtained by measuring a bloodshot degree of eyeballs of the user in accordance with the one image data.

Further, one important construction disclosed in the present specification is an information processing system for transmitting and receiving information of a user to and from another information processing system through a transmission line, the system comprising, a camera for obtaining one image data representing an expression of a face of the user and another image data representing a movement of a mouth of the user, a microphone for obtaining voice data of the user, means for storing the one image data in advance, means for detecting a degree of tiredness of the user by image-processing the stored one image data, and changing the stored one image data for synthesizing image data in accordance with the degree of tiredness of the user, wherein the synthesizing image data is obtained by synthesizing the stored one image data with the another image data, and means for transmitting the voice data and one of the stored one image data and the synthesizing image data to the another information processing system, wherein the degree of tiredness of the user is obtained by measuring a current bloodshot degree of eyeballs of the user and identifying the user in accordance with the one image data, referring to reference image data having a reference bloodshot degree in accordance with the identification, and comparing the current bloodshot degree of the eyeballs of the user with the reference bloodshot degree.

Further, one important construction disclosed in the present specification is an information processing system for transmitting and receiving information of a user to and from another information processing system through a transmission line, the system comprising, a camera for obtaining one image data representing an expression of a face of the user and another image data representing a movement of a mouth of the user, a microphone for obtaining voice data of the user, means for storing the one image data in advance, means for detecting a degree of tiredness of the user by image-processing the stored one image data, and changing the stored one image data for synthesizing image data in accordance with the degree of tiredness of the user, wherein the synthesizing image data is obtained by synthesizing the stored one image data with the another image data, and means for transmitting the voice data and one of the stored one image data and the synthesizing image data to the another information processing system wherein the degree of tiredness of the user is obtained by measuring a current bloodshot degree of eyeballs of the user and identifying the user with an ID number, referring to reference image data having a reference bloodshot degree in accordance with the identification, and comparing the current bloodshot degree of the eyeballs of the user with the reference bloodshot degree.

In other words, one of the important inventions disclosed in the present specification is an information Processing system provided with a camera and a microphone, wherein the degree of tiredness of the user is estimated by obtaining the bloodshot degree of the eyeballs of the user from image data taken in by the camera, and wherein if this exceeds a certain fixed value, the actual image data of the user are not transmitted but image data which are a combination of the movement of the mouth of the user and image data which have been taken and stored in advance are transmitted.

Further, one important construction disclosed in the present specification is an information processing system for transmitting and receiving information of a user to and from another information processing system through a transmission line, the system comprising a camera for obtaining image data of the user including background data, a microphone for obtaining voice data of the user, means for storing desired background data, means for changing the background data for the desired background data by image processing, and means for transmitting the image-processed image data and the voice data to the another information processing system.

Further, one important construction disclosed in the present specification is an information processing system for transmitting and receiving information of a user to and from another information processing system through a transmission line, the system comprising, a camera for obtaining image data including a face of the user, a microphone for obtaining voice data of the user, means for making up the face of the user included in the image data by image processing, and means for transmitting the image-processed image data and the voice data to the another information processing system.

Further, one important construction disclosed in the present specification is an information processing system for transmitting and receiving information of a user to and from another information processing system through a transmission line, the system comprising, a camera for obtaining image data of the user including face data and background data, a microphone for obtaining voice data of the user, means for storing desired background data, means for making up the face data of the image data and changing the background data for the desired background data by image processing, and means for transmitting the image-processed image data and the voice data to the another information processing system.

In other words, another important invention disclosed by the present specification is an image processing system provided with a camera and a microphone, wherein the background is changed arbitrarily by the selection of the user, and the image data of the background of the user which is to be transmitted to another information processing system is changed.

BRIEF DESCRIPTION OF THE DRAWINGS

FIGS. 4 to 6 show a flowchart for image processing.

DETAILED DESCRIPTION OF THE PREFERRED EMBODIMENTS

Figure 1:
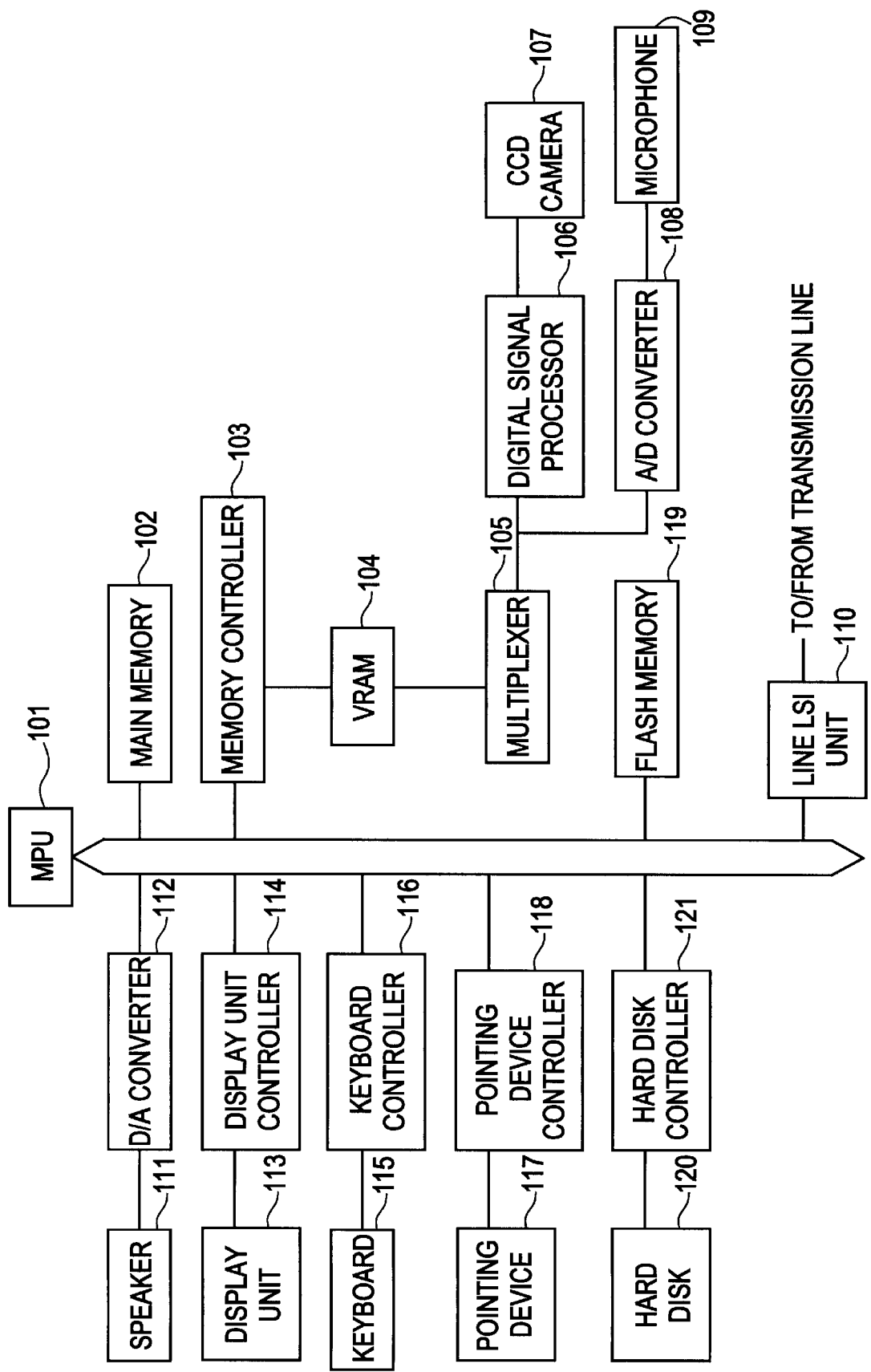
FIG. 1 shows a block diagram of an information processing system which is provided with a camera and a microphone and performs image processing.
Figure 3:
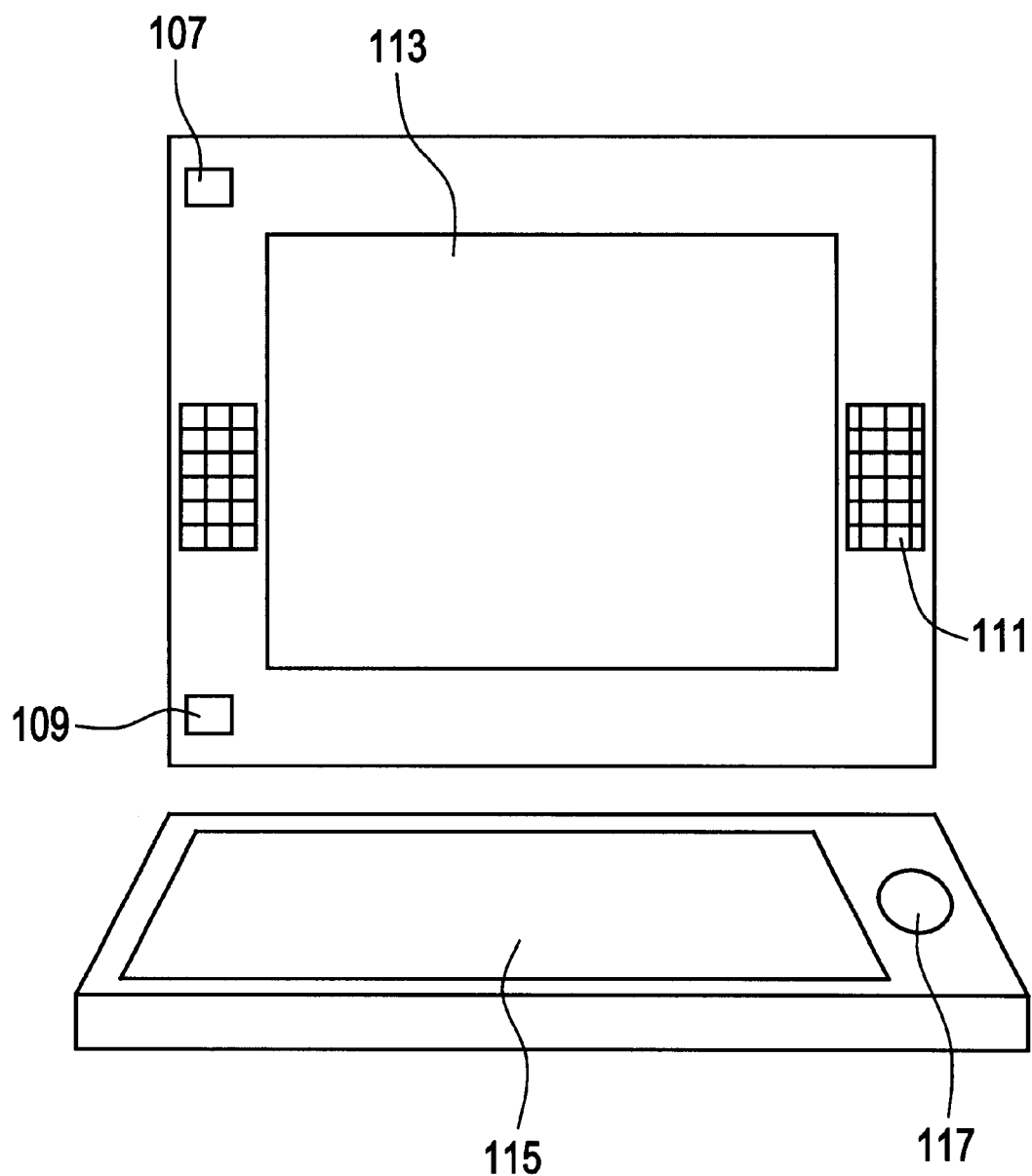
FIG. 3 shows an example of the external construction of an information processing system.

FIG. 1 shows a block diagram of an information processing system of the present embodiment, and FIG. 3 shows the external construction of the information processing system. This is an example of a PC (personal computer) or WS (workstation) which is provided with a CCD (charge coupled device) camera and a microphone.

The embodiment information processing system includes a micro processing unit (MPU) 101, a main memory 102, a memory controller 103, a video random access memory (VRAM) 104, a multiplexer 105, a digital signal processor (DSP) 106, CCD camera 107, an A/D converter 108, a microphone 109, a line large scale integrated (LSI) unit 110, a speaker 111, a D/A converter 112, a display unit 113, a display unit controller 114, a keyboard 115, a keyboard controller 116, a pointing device 117, a pointing device controller 118, a flash memory 119, a hard disk 120 and a hard disk controller 121.

The MPU 101 controls the entire system, such as controls of the memory controller 103, the line LSI unit 110 and the like.

The main memory 102 is used for image-processing the image data representing the face of a user and the like obtained by the CCD camera 107. That is, image processing is performed in the main memory 102 by the MPU 101 to detect the degree of tiredness from the expression of the user included in the image data. The memory controller 103 performs the refresh operation and the read/write operation control for the VRAM 104, and transfers data stored in the VRAM 104 to the main memory 102 by direct memory access (DMA) transfer. In the VRAM 104, the image data and the voice (sound) data of a user are stored.

The multiplexer 105 selects image data obtained by the CDD camera 107 or the voice data obtained by the microphone.

The CCD camera 107 obtains the image data of a user. The obtained image data (video signal) is binarized by the digital signal processor 106 and then is stored in the VRAM 104.

The microphone 109 obtains the voice of a user as a voice signal. The A/D convertor 108 digitizes the voice signal. The voice data is stored in the VRAM 104 through the multiplexer 105.

The line LSI unit 110 operates as an interface for an external line and transmits the image data and the voice data by DMA transfer to the destination using a packet format defined by the protocol of the external line. Also, the unit 110 receives image data and voice data of another user from the destination.

In the present embodiment, with an intelligent option board or a dumb option board connected to the bus of the PC or WS, it is also possible to control the peripheral circuits directly from the CPU (central processing unit) of the PC or WS.

The speaker 111 mainly outputs, through the D/A converter 112, the voice data of another user transmitted from another information processing system, to regenerate the voice of the transmitting user as the another user.

The display unit 113 mainly displays image data of another user transmitted from another information processing system, under control of the display unit controller 114.

The keyboard 115 is controlled by the keyboard controller 116 for key input control and used to key-input various information such as ID information of users.

The pointing device 117 includes a mouse, a ball or the like and is controlled by the pointing device controller 118.

In such information processing system, the image data obtained by the CCD camera 107 is image-processed if necessary and then transmitted to another information processing system.

Figure 4:
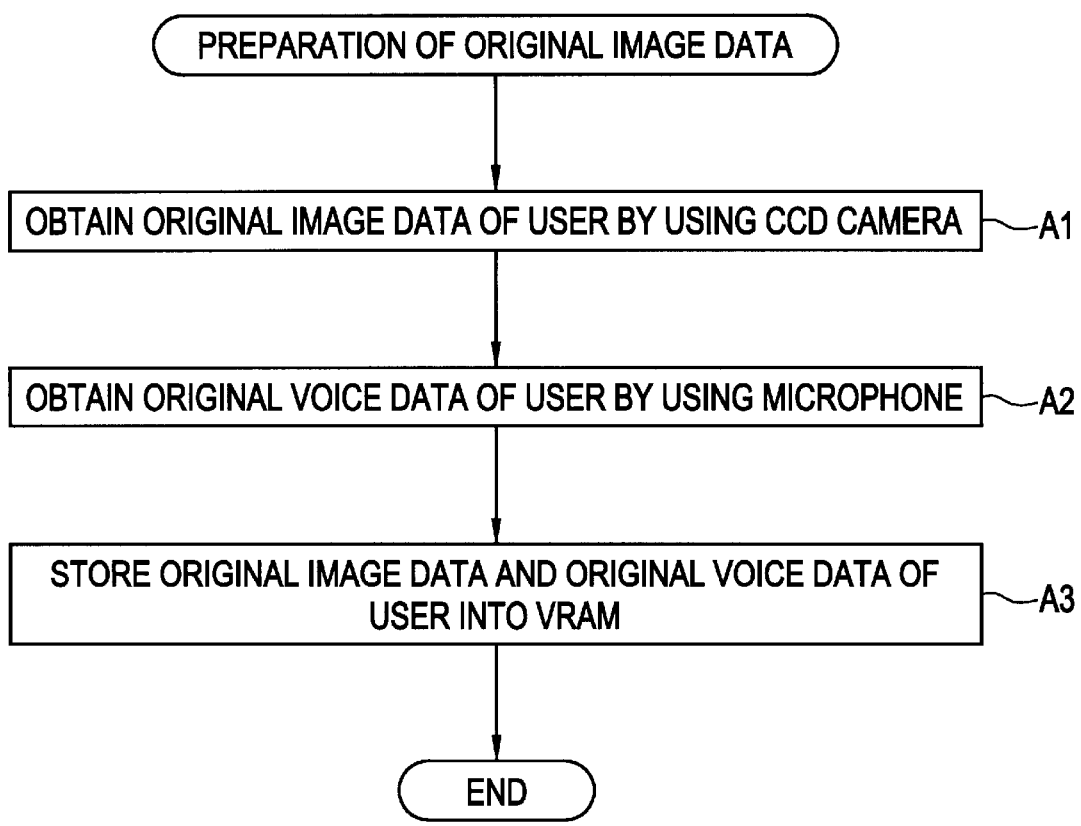
Figure 5B:
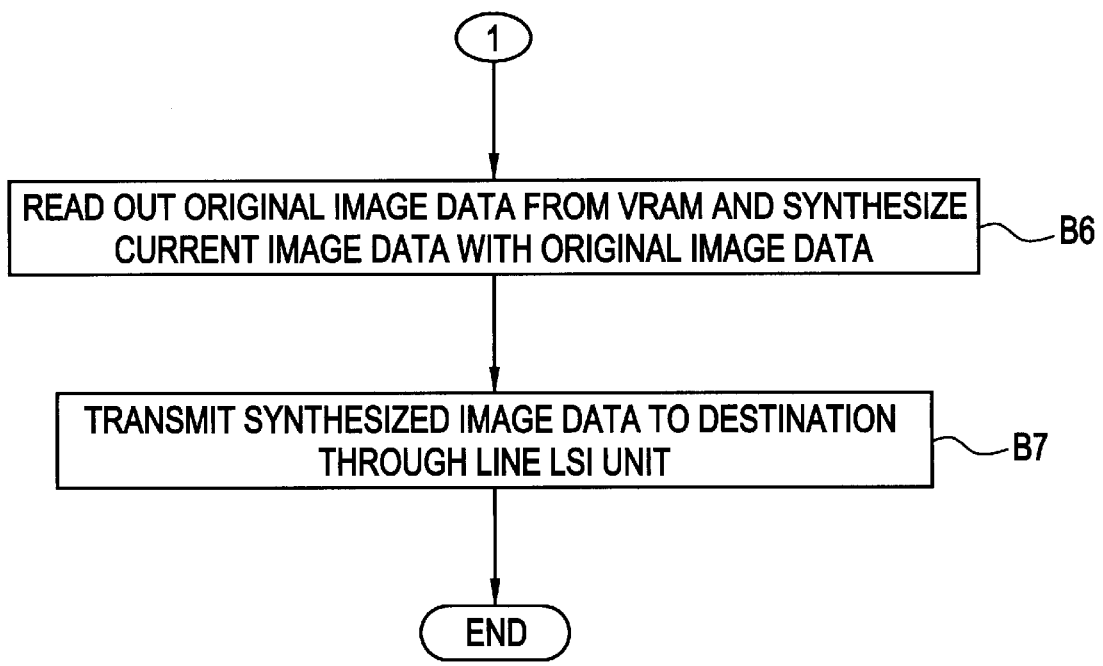
Figure 5C:
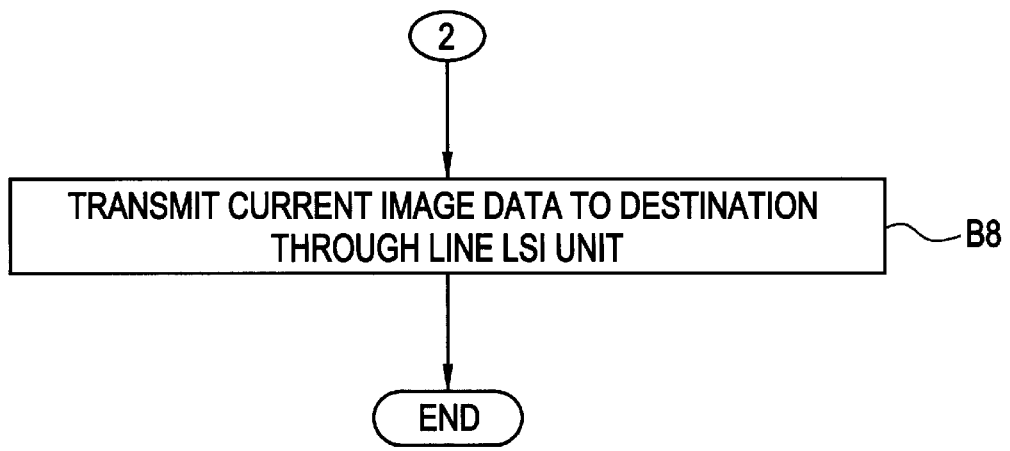

An operation of the information processing system will be described with FIGS. 4 to 6.

To prepare the communication to the user of another information processing system, image data representing a face of a user and the like and voice data is obtained in the present system in advance. That is, the image data (original image data) of the user is obtained by the CDD camera 107 (step A1). The obtained image data (video signal) is binarized by the digital signal processor 106 and then stored in the VRAM 104 (step A3). Also, at the same time, voice data (original voice data) of the user is obtained by the microphone 109 (step A2). The obtained voice data (analog signal) is digitized by the AD converter 108 and then stored in the VRAM 104 (step A3).

When the communication is requested by another user of another information processing system, the image data of the user and the like in the present system is transmitted by the following operation.

First, a plurality of current image data of the user are obtained by the CCD camera 107 during a desired period of time (step B1) and then stored in the VRAM 104 through the digital signal processor 106 and the multiplexer 105. In the MPU 101, the following processes are performed in accordance with an image-processing program to be stored in advance. That is, in step B2, an eye portion of the user is extracted from the obtained current image data.

In step B3, it is determined whether an edge of the extracted eye portion is detected or not. If the edge is detected, it can be determined that the eyes were closed, that is, the user blinked. The determination is performed for each extracted eye portion, and the number of eyewinks (blinks) of the user is counted (step B4).

In step B5, it is determined that a count value counted by the step B4 is greater than or equal to a desired value. That is, it is determined whether or not the number of blinks of the user during a desired time is no less than the desired number of blinks. This is based on the matter that there is the number of blinks as a parameter representing the degree of tiredness of a human and the number of blinks increases in accordance with the increase of the degree of the tiredness.

In step B5, when the count value is greater than or equal to the desired value, it is determined that the user is tired. Therefore, the original image data of the user stored in the step A3 in advance is read out from the VRAM 104, and the current image data is synthesized with the original image data (step B6). The synthesized image data is transmitted to the destination of another information processing system through the line LSI unit 110 (step B7).

On the other hand, in step B5, when the count value is smaller than the desired value, it is determined that the user is not tired. Therefore, the current image data is transmitted to the destination of another information processing system through the line LSI unit 110 without image synthesizing (step B8).

The above image-processing is performed in th main memory 102 by the MPU 101. At this time, the number of blinks of the user during a desired period is calculated by the MPU 101. Then, when the number of blinks is no less than a desired value, an image of the user stored in advance in the hard disk 120, the flash memory 119 or the like is synthesized with the mouth portion of the current image of the user. The synthesized image is DMA-transferred by the line LSI unit 110, thereby to transmit the image data to the transmission line. Therefore it is possible to transmit image data just as though the user is speaking with the clothes and the background stored in advance.

As a parameter representing the degree of tiredness, other than the number of blinks, the bloodshot degree can be used. In this case, for example, the following processing is performed in the present system.

First, a plurality of current image data of the user are obtained by the CCD camera 107 during a desired period of time (step C1) and then stored in the VRAM 104 through the digital signal processor 106 and the multiplexer 105. In the MPU 101, the following processes are performed in accordance with an image-processing program to be stored in advance. That is, in step C2, an eye portion of the user is extracted from the obtained current image data.

In step C3, a bloodshot portion is detected from the extracted eye portion. Since the bloodshot portion may be red, when the degree of red in a portion is greater than a desired level, it is determined that the portion is a bloodshot portion, and the portion is detected as the bloodshot portion. Further, an area ratio of the bloodshot portion to the eye portion is measured (step C4). The area ratio is used as an index for determining the bloodshot degree of the user.

In step C5, it is determined that the area ratio of the bloodshot portion is greater than or equal to a desired value. When the area ratio of the bloodshot portion is no less than the desired value, it is determined that the user is tired. Therefore, the original image data of the user stored in the step A3 in advance is read out from the VRAM 104, and the current image data is synthesized with the original image data (step B6). The synthesized image data is transmitted to the destination of another information processing system through the line LSI unit 110 (step B7).

On the other hand, in step B5, when the area ratio of the bloodshot portion is smaller than the desired value, it is determined that the user is not tired. Therefore, the current image data is transmitted to the destination of another information processing system through the line LSI unit 110 without image synthesizing (step B8).

Therefore it is possible to transmit image data just as though the user is speaking with the clothes and the background stored in advance.

The synthesizing may also be effected for not only the mouth but also for the whole of the face, including the movement of eyes and skin. Also, it is possible to transmit to the other party not a tired expression but synthesizing of a healthy, bright expression with the current movement of the mouth, or an expression involving movement of the eyes and skin, for example, and thereby render a pleasant sensation to the other party in the communication.

Identification of the user may be performed by comparing the obtained image with a stored image, and it may also be performed by providing a user ID to each user to be input.

As described above, by changing the images obtained by the camera into images obtained by the user in advance using the system, and synthesizing these images to form the image of the user to be transmitted, according to the state of the user, it is possible to avoid transmitting of images which the user does not wish to transmit, and to transmit the expression of the user clearly to the other party. It is thus possible to maintain privacy and to transmit an image which is not impolite to the other party.

A description will now be given relating to the basic method of image processing.

The image processing apparatus converts the input image into a binary image by binarization. The binarization sets a value of 1 if the brightness is a fixed value (threshold value) or more, and sets 0 otherwise. The threshold value can be determined by the following methods.

(1) In a fixed threshold value method, the threshold value is set in advance. This method can be used if the variations in the image is less and the image has at least sufficient contrast.

(2) A p tile method is effective if the ratio of "1" portions within the image is known in advance. Normally, a brightness histogram is taken, and the threshold value is set to a brightness such that the cumulative distribution is p percent. Even if the histogram is not produced in advance, it is possible to obtain a threshold value which gives approximately p percent by binarizing using a suitable threshold value, by repeating obtaining of the ratio of "1".

(3) In a mode method, if the brightness histogram is bimodal, the value of the brightness in the troughs is taken as the threshold value. There also exists a variable threshold value method in which a fixed threshold value is not applied to the whole image, but the image is divided into regions, and threshold values are determined by the mode method for the divided regions.

(4) In a floating binarization and moving average threshold value method, if the amplitude of the brightness signal is attenuated and the delayed signal is set as the threshold value, it is possible to detect sudden variations in brightness. A similar method which is also used is a moving average method in which the average brightness over a fixed period is set as the threshold value.

Figure 2:
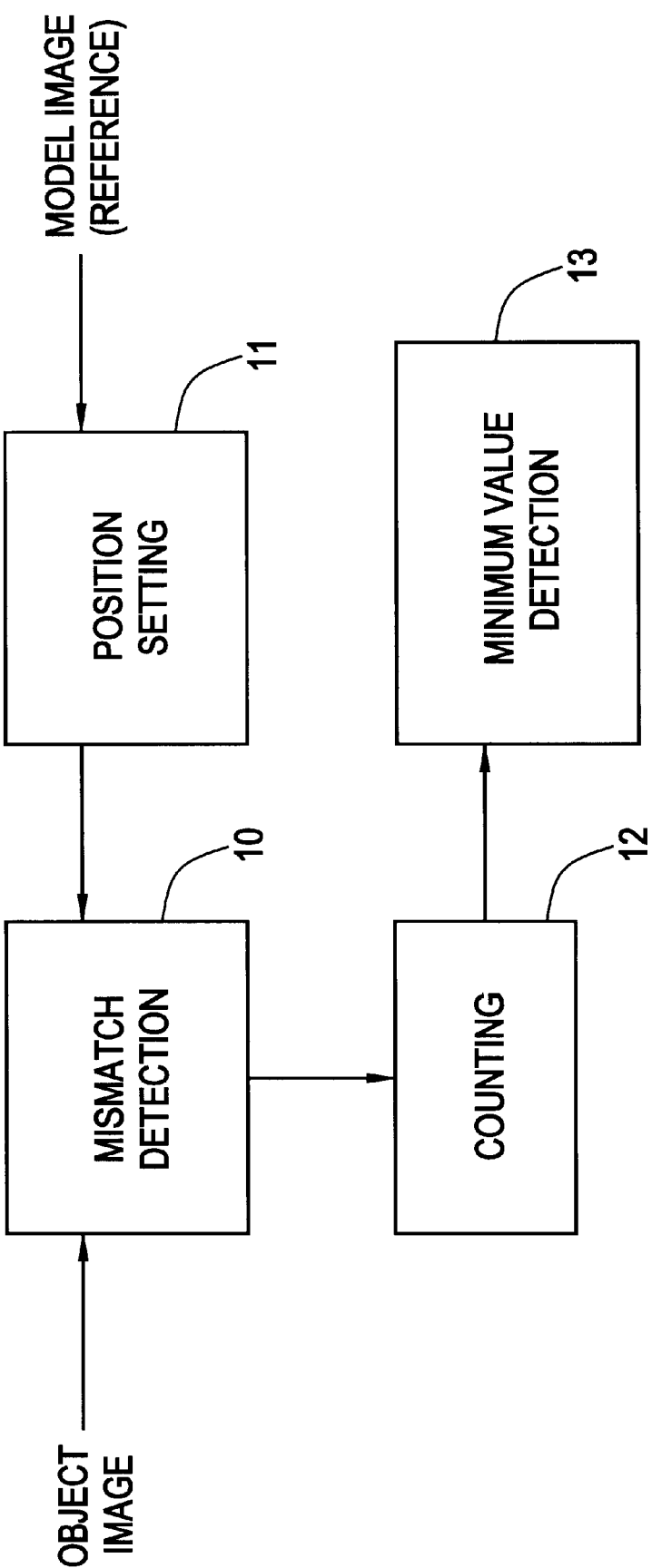
FIG. 2 shows the principle of pattern matching in image processing.

FIG. 2 shows the principle of pattern matching whereby the location of a particular pattern is detected. The object image is made into a binary image, and the region to be detected is set as "1". This region is set at a suitable position on the image, and the degree of overlap with the object image is examined in a mismatch detection block 10. A plurality of positions are set in a position setting block 11. If the overlap is detected in the positions, counting is performed in a counting block 12. A count value is detected in a minimum value detection block 13. The position of the pattern is obtained when the degree of overlap is maximum and the degree of mismatch is small. If the degree of mismatch is not small in any position then such a pattern is deemed not to be present.

If the two-dimensional pattern of the object is not constant, simple pattern matching is insufficient. Various features must be extracted from the image and determination made based on a combination thereof. A feature obtained from one portion of the image is called a local feature, and subsequent processing is often performed based on this.

To obtain what is shown in the image, it is necessary to extract features from the image, produce a description of the object and match this with a previously formed model. Features include points, lines and regions and a number of levels. That is, features can be extracted from only a small local region, or they can reflect the state of a larger region. Further, features can be expressed in a layered manner such that points are joined together to form lines, and regions enclosed by lines are obtained. For each feature, which level is suitable depends on the purpose.

Space differential is often used to perform extraction from a graded image or an edge which is part of the boundary between two regions with different brightnesses. In order to obtain the difference of the brightness at a certain point and the direction thereof, the gradient of the brightness $f(x, y)$ should be calculated. If $f(x, y)$ is a continuous image, the gradient grad $[f(x, y)]$ is a two-dimensional vector indicated by formula (1).

$$\text{grad}[f(x,y)] = (\partial f(x,y)/\partial x, \partial f(x,y)/\partial y) \tag{1}$$

If the absolute value is large, there is an edge and the perpendicular direction is taken as the gradient. However, if the width of the line is large to some extent then if the direction has two opposite gradients, this can be taken to be the boundary of the line. Further, if the width of the line is small, the Laplacian of formula (2) can be used.

$$\Delta^2 f(x,y) = \partial^2 f(x,y)/\partial x^2 + \partial^2 f(x,y)/\partial y^2 \tag{2}$$

If the value of the Laplacian is large, this point is darker than the rest, and if it is negative then it is brighter than the rest.

To extract a single line by joining edges or line elements, the line elements are obtained, the image is divided into small regions of 4×4 pixels, and the largest differential values from the edge points (edge elements) within each small region are left and the others are erased. The direction of an edge is obtained by examining the brightness in the vicinity of each edge point. If the edge direction within adjacent small regions is approximately the same, the two edge points are joined. Points which are not connected at all are deemed to be noise and are erased. At each stage of this process, only the vicinity of the image is used, and furthermore processes for each point are independent of the processes for other points. Such processing is known as local processing, and it is possible to perform processing in parallel for each point.

To detect a line by performing local processing a number of times, there are methods which use probability as described below. First, by detecting edge points, the strength of the edge point (absolute value of differential) and direction are obtained. An initial value for the probability that each edge point is on a line is determined based on the strengths of the edge points. Next, the probability for each edge point is changed by the strength and direction of neighboring edge points. If a certain edge point and a different edge point in the vicinity have the same direction, the probability of the edge point is increased. If the directions differ greatly, it is reduced. By performing such correction a number of times, gradually noise is erased and the probability of an edge point being on a line approaches 1. The process is known as the relaxation method.

In the parametric space method, a straight line is represented by $\rho = x \cos \theta + y \sin \theta$. If the coordinates $(x_i, y_i)$ of the resulting boundary points are converted to a $\theta$-$\rho$ plane, a curved line in this plane, indicated by $\rho = x_i \cos \theta + y_i \sin \theta$ is obtained. If all of the boundary points within a scene are converted, all points on the same straight line pass through one point in the $\theta$-$\rho$ plane. Thus if a point $(\theta_0, \rho_0)$ through which a large number of curves passes is obtained, the equation for the straight line can be obtained. If the direction of the boundary points is known, the straight line can be determined from a histogram relating to $\rho$. The parameter method requires a special histogram to be produced with the same number of dimensions as the number of unknown parameters, and is therefore difficult to apply to a curved line. However, it is effective if there are fixed constraints on the parameters included in the equation for the curved line, and the dimensions of the parameter space can be reduced to two or less.

The tracking method is applicable to obtain a general curve. The tracking method is a process whereby lines are produced connecting adjacent edge points. The following procedure is required to perform tracking.

(1) Detect the point at which tracking is to begin.

(2) Estimate the position, and in some cases the direction, of the adjacent edge point.

(3) Detect an edge point based on this estimation.

(4) Determine whether to continue tracking or to finish tracking.

Tracking involves serial processing, in contrast to local processing. Therefore if a single edge point is to be detected, this process depends on the result of previous processing. Therefore the obtained result will be different depending on where in the image the processing starts. However, with serial processing, it is probable that processing can be performed effectively by using previously obtained information effectively.

A method for extracting uniform regions is known as the region method, and include the following two processes.

(1) In a region method using merging, firstly, a large number of small regions are produced, and similar regions are merged.

(2) In a region method using division, starting with a single region, this is divided into regions with different characteristics.

The region method using merging initially obtains small regions in which the brightness is approximately the same, known as base regions. Regions are gradually merged based on the difference between the brightnesses of two adjacent regions, the length of the boundary and the shape of the regions. This process is repeated until no more regions can be merged.

The method using division has the important problem of determining on what basis the image should be divided. Dividing a color image based on the histograms of various properties is effected as follows. Firstly, the red state, green state, blue state, brightness, color phase, saturation, and the Y, I and Q color television signals are detected for each pixel. Nine types of histogram are produced from the parameters, and the parameters which form conspicuous peaks and troughs are selected, and divisions are made to the left and right of troughs, which are used as boundaries. The image is divided depending on which properties the pixels have. The various histograms are then produced for the divided regions, and these are once again divided more finely. This process is repeated until it is no longer possible to make divisions.

The region method using division is effective if it is possible to use not simply brightness, but a relatively large amount of information, as in this example. However, it is not necessary to use as many as 9 types, as in this example.

By using the above methods, it is possible, after obtaining the image data of the user, to determine whether or not the user has blinked, and to calculate the bloodshot degree of the eyeballs of the user. In the present embodiment, the eyeballs of the user is monitored using a CCD camera, but the direction of gaze of the eyeballs, or the reaction of the pupils may also be observed using a goggle-type head-up display device.

In the embodiment, it is shown in a case wherein the clothes and the background are changed. However, if it is determined that the user is extremely tired, then it is possible to change the actual expression of the user by image processing, and to transmit to the other information processing system the image data which synthesizes a bright, healthy face from a time at which the user was in good health. Further, at this time is also advantageous to control the tone or pitch of the voice slightly such that if the pitch of the voice is liable to be lowered, for example if the user is extremely tired, a bright voice is formed.

The information processing system according to the present invention is provided with a camera and a microphone, and makes it possible to protect the privacy of parties involved in communication when performing data communication by image data, by synthesizing image data obtained by the camera with image data stored in advance, either based on a determination made from the image data, or at the will of the transmitting party in the communication, and thus making the clothes, hair, background, make-up etc. different from reality, and transmitting these data to the other party in the communication.

What is claimed is:

1. A videophone comprising:
   a camera for obtaining image data of a user of said videophone;
   a microphone for obtaining voice data of the user;
   means for detecting a degree of tiredness of the user;
   means for modifying said image data by image processing;
   means for transmitting the image-processed image data and the voice data to another videophone remote from said videophone; and
   a goggle-type head-up display device for displaying an image from another videophone to be viewed by said user.

2. A videophone according to claim 1 wherein said image data includes background data.

3. The videophone according to claim 1 further comprising means for modifying the voice data in accordance with said degree of tiredness.

4. The videophone according to claim 1 wherein said image data is modified in accordance with said degree of tiredness.

5. The videophone according to claim 1 wherein said tiredness is determined based on detecting the number of blinks of an eyeball of the user or a bloodshot degree.

6. The videophone according to claim 1 wherein said tiredness is determined based on detecting a bloodshot degree of an eyeball of the user.

7. A videophone comprising;
   a camera for obtaining image data of a user of said videophone including background data;
   a microphone for obtaining voice data of the user;
   means for detecting a degree of tiredness of the user;
   means for storing desired background data;
   means for changing the background data for the desired background data by image processing;
   means for transmitting the image-processed data and the voice data to another videophone remote from said videophone; and
   a goggle-type head-up display device for displaying an image from another videophone to be viewed by said user.

8. The videophone according to claim 7 further comprising means for modifying the voice data in accordance with said degree of tiredness.

9. The videophone according to claim 7 wherein said background data is modified in accordance with said degree of tiredness.

10. The videophone according to claim 7 wherein said tiredness is determined based on detecting the number of blinks of an eyeball of the user or a bloodshot degree.

11. The videophone according to claim 7 wherein said tiredness is determined based on detecting a bloodshot degree of an eyeball of the user.

12. A videophone comprising:
   a camera for obtaining image data of a user of said videophone;
   a microphone for obtaining voice data of the user;
   a processor for modifying at least the image data;
   means for detecting a degree of tiredness of the user;
   transferring means for transmitting the modified image data and the voice data to another instrument remote from said videophone; and
   a goggle-type head-up display device for displaying an image from said instrument to be viewed by said user.

13. A videophone according to claim 12 wherein said image data includes background data.

14. The videophone according to claim 12 further comprising means for modifying the voice data in accordance with said degree of tiredness.

15. The videophone according to claim 12 wherein said image data is modified in accordance with said degree of tiredness.

16. The videophone according to claim 12 wherein said tiredness is determined based on detecting the number of blinks of an eyeball of the user or a bloodshot degree.

17. The videophone according to claim 12 wherein said tiredness is determined based on detecting a bloodshot degree of an eyeball of the user.

18. A videophone comprising:
   a camera for obtaining image data of a user of said videophone;
   a microphone for obtaining voice data of the user;
   a converter for digitizing said image data and said voice data of the user;
   a processor for modifying at least the digitized image data;
   means for detecting a degree of tiredness of the user;
   transferring means for transmitting the modified image data and the voice data to another instrument remote from said videophone; and
   a goggle-type head-up display device for displaying an image from said instrument to be viewed by said user.

19. A videophone according to claim 18 wherein said image data includes background data.

20. The videophone according to claim 18 further comprising means for modifying the voice data in accordance with said degree of tiredness.

21. The videophone according to claim 18 wherein said digitized image data is modified in accordance with said degree of tiredness.

22. The videophone according to claim 18 wherein said tiredness is determined based on detecting the number of blinks of an eyeball of the user or a bloodshot degree.

23. The videophone according to claim 18 wherein said tiredness is determined based on detecting a bloodshot degree of an eyeball of the user.

24. A videophone comprising:
   a camera for obtaining image data of a user of said videophone;
   a microphone for obtaining voice data of the user;
   a converter for digitizing said image data and said voice data of the user;
   a memory for storing the digitized image data and the digitized voice data;
   a processor for modifying at least the digitized image data;
   means for detecting a degree of tiredness of the user;
   transferring means for transmitting the modified image data and the voice data to another instrument remote from said videophone; and
   a goggle-type head-up display device for displaying an image from said instrument to be viewed by said user.

25. A videophone according to claim 24 wherein said image data includes background data.

26. The videophone according to claim 24 further comprising means for modifying the voice data in accordance with said degree of tiredness.

27. The videophone according to claim 24 wherein said digitized image data is modified in accordance with said degree of tiredness.

28. The videophone according to claim 24 wherein said tiredness is determined based on detecting the number of blinks of an eyeball of the user or a bloodshot degree.

29. The videophone according to claim 24 wherein said tiredness is determined based on detecting a bloodshot degree of an eyeball of the user.

* * * * *